United States Patent
Kumar et al.

(10) Patent No.: US 11,654,173 B2
(45) Date of Patent: May 23, 2023

(54) PURIFIED XANTHOPHYLL COMPOSITION COMPRISING (TRANS,R,R)-LUTEIN AND(TRANS,R,R)-ZEAXANTHIN AND PROCESS FOR THE PREPARATION THEREOF

(71) Applicant: OMNIACTIVE HEALTH TECHNOLOGIES LIMITED, Maharashtra (IN)

(72) Inventors: Sunil T.K. Kumar, Pune (IN); Laxman Sawant, Pune (IN); Mohan Lal Jangir, Pune (IN)

(73) Assignee: OMNIACTIVE HEALTH TECHNOLOGIES LIMITED, Mumbai (IN)

( * ) Notice: Subject to any disclaimer, the term of this patent is extended or adjusted under 35 U.S.C. 154(b) by 127 days.

(21) Appl. No.: 17/275,195

(22) PCT Filed: Sep. 21, 2019

(86) PCT No.: PCT/IB2019/058007
§ 371 (c)(1),
(2) Date: Mar. 11, 2021

(87) PCT Pub. No.: WO2020/065484
PCT Pub. Date: Apr. 2, 2020

(65) Prior Publication Data
US 2021/0322502 A1    Oct. 21, 2021

(30) Foreign Application Priority Data
Sep. 26, 2018    (IN) .............................. 201821036199

(51) Int. Cl.
A61K 36/28    (2006.01)
A61K 31/047   (2006.01)

(52) U.S. Cl.
CPC ............ *A61K 36/28* (2013.01); *A61K 31/047* (2013.01); *A61K 2236/333* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| 6,743,953 B2 * | 6/2004 | Kumar T. K. ........ C07C 403/24 568/816 |
| 8,425,948 B2 * | 4/2013 | Sethuraman .............. A61P 9/10 424/725 |
| 9,889,173 B2 * | 2/2018 | Xu .......................... A61K 33/00 |
| 2011/0065805 A1 * | 3/2011 | Kumar T.K. .......... A61K 31/047 426/429 |
| 2011/0282083 A1 * | 11/2011 | Reilly ................... C07C 403/24 549/547 |
| 2018/0078644 A1 * | 3/2018 | Eidenberger ............ A61P 27/02 |

FOREIGN PATENT DOCUMENTS

MX    9909568    *    4/2001

* cited by examiner

*Primary Examiner* — Ralph J Gitomer
(74) *Attorney, Agent, or Firm* — IP Pundit LLC

(57) ABSTRACT

The invention relates to a purified xanthophyll composition comprising (trans,R R)-lutein and (trans,R,R)-zeaxanthin, which is comprised of more than 80% of total xanthophylls and a process for the preparation thereof. Purified xanthophyll composition is comprised of selective isomers such as at least 85% by weight of (trans,R,R)-lutein and at least 15% by weight of (trans,R,R)-zeaxanthin. The composition is prepared by process of extraction from two different plant sources using industrially viable process and purified by employing food grade polar and non-polar solvents. The invention relates to purified xanthophyll composition which is selectively free from (R,S)-zeaxanthin and is suitable for human consumption.

9 Claims, 2 Drawing Sheets

PURIFIED XANTHOPHYLL COMPOSITION COMPRISING (TRANS,R,R)-LUTEIN AND(TRANS,R,R)-ZEAXANTHIN AND PROCESS FOR THE PREPARATION THEREOF

CROSS REFERENCE TO RELATED APPLICATIONS

This application is a national phase application under 35 U.S.C. § 371 of International Application No. PCT/IB2019/058007, filed on Sep. 21, 2019, which claims priority to Indian Patent Application No. 201821036199, filed on Sep. 26, 2018; the disclosures of all of which are hereby incorporated by reference in their entirety.

FIELD OF INVENTION

The invention relates to a purified xanthophyll composition comprising (trans,R,R)-lutein and (trans,R,R)-zeaxanthin and a process for the preparation thereof. The invention specifically relates to a xanthophyll composition comprised of more than 80% of total xanthophylls, which is selectively comprised of isomers such as (trans, R,R)-lutein and (trans, R,R)-zeaxanthin. The invention more specifically relates to the purified xanthophyll rich composition comprised of at least 85% by weight of (trans,R,R)-lutein and at least 15% by weight of (trans,R,R)-zeaxanthin, which is prepared by process of extraction from two different plant sources using industrially viable purification process and food grade solvents. The process can be comprised of mixing the plant concentrates rich in xanthophyll esters in definite proportion and subjecting to treatment with alcoholic alkali, followed by neutralization and purification process to get a xanthophyll rich composition. The purification process may be comprised of treatment of crude xanthophylls with food grade solvent like ethyl acetate and washing with polar solvent to get purified xanthophyll composition comprised of isomers such as (trans,R,R)-lutein and (trans,R,R)-zeaxanthin. The invention relates to purified xanthophyll composition which is free from (R, S) & (S,S)-zeaxanthin isomers and is suitable for human consumption to be used in various eye health applications.

BACKGROUND

Lutein and zeaxanthin isomers are antioxidant carotenoids found in the human retina and macula. These carotenoids have a protective effect against photo-induced damage to the lens and the retina. Two of the major mechanisms of protection offered by lutein and zeaxanthin against age-related blue light damage, cataract and macular degeneration are the quenching of singlet oxygen and other reactive oxygen species and the absorption of blue light. Their consumption in right amounts can prevent visual impairment and acquired blindness in millions of aging population. Thus nutrition is one promising way to prevent or delay the progression of these ocular diseases. Green leafy vegetables, as well as other foods such as eggs, contain important nutrients such as lutein and (R,R)-zeaxanthin; while meso-zeaxanthin is found only in sea-creatures. Human body does not naturally synthesize required amounts of lutein and zeaxanthin. Therefore getting daily amounts of lutein and zeaxanthin through regular diet or nutritional supplements can help maintain good eye health.

U.S. Pat. No. 8,425,948 provides for a process for isolation of carotenoid crystals comprising drying a plant part to obtain a meal. The oleoresin is further enriched with alcohol and hydrolyzed with alcoholic alkali to obtain reaction mixture and extracting the meal with alcohol to obtain a reaction mixture. Carotenoids crystals are precipitated from reaction mixture by adding hot water and dried to get a product which is comprised of lutein and zeaxanthin in a ratio of about 10:1 or 5:1 or 1:1. All the examples of the patent indicate that the product is obtained from a single plant Marigold by extraction and enrichment of the oleoresin and the end product carotenoid crystals is comprised of all trans-lutein and all trans-zeaxanthin. However there is no further information about amount of individual isomers (trans,R,R)-zeaxanthin and (R,S)-zexanthin in the resulting product.

U.S. Pat. No. 6,504,067 relates to a process to obtain xanthophyll concentrates from plant extracts, comprising: refining the plant extracts by treating them with a diluted alkali, followed by treating them with a diluted organic or inorganic acid. This extract was subsequently saponified and precipitated to obtain xanthophyll concentrate comprising mainly trans-lutein and trans-zeaxanthin. Further purification of xanthophyll concentrate was carried out by means of hexane.

U.S. Pat. No. 9,889,173 discloses a composition for treatment or prevention of age-related macular degeneration, comprising effective amounts of lutein, zeaxanthin and epigallocatechin gallate, wherein the weight ratio of zeaxanthin to lutein is in a range of 2:1-3:1. This reference particularly highlights the synergistic combination of macular carotenoids and tea extract.

CN106692187 provides a composition for improving visuognosis persistence and protecting eye health, wherein the composition comprises lutein, (3R,3'R)-zeaxanthin,(3R, 3'S,meso)-zeaxanthine, docosahexaenoic acid (DHA), trace element zinc, copper and vitamin B. This patent reference also highlights the synergistic combination of macular carotenoids and docosahexaenoic acid along with minerals and vitamins.

In view of above, the references claim the compositions comprising macular carotenoids such as lutein and all trans-zeaxanthin, which can be obtained by extraction of plant with solvent like alcohol and further enrichment of the extract before subjecting to the saponification and precipitation of the carotenoid crystals. However there are no references which claim a composition which is comprised of combination of selective (trans,R,R)-isomers of lutein and zeaxanthin in specific percentage, which is prepared by controlled conversion of xanthophyll esters followed by purification. The composition prepared in this way, which is rich in xanthophyll content and is comprised of (trans,R,R)-lutein and (trans,R,R)-zeaxanthin in specific percentage is nowhere reported in the prior art and very useful for applications in Eye Health.

SUMMARY

The inventors of instant invention have carried out rigorous experimentation to prepare a purified xanthophyll composition which is comprised of selective isomer of zeaxanthin in combination with trans-lutein, which is prepared from extraction of two different plant sources and subjecting the xanthophyll ester concentrate to treatment with alcoholic alkali. The resulting reaction mixture is then subjected to specific isolation and purification process such as neutralization and use of food grade polar and non-polar solvents to selectively get at least 15% by weight of (trans, R,R)-zeaxanthin in combination with (trans-R,R)-lutein in a purified xanthophyll composition. There are no references till date which report purified xanthophyll composition comprising of selective isomer of zeaxanthin along with lutein, which is prepared by using food grade solvents and industrially viable process.

Thus the invention relates to a purified xanthophyll composition comprising selective isomers such as (trans,R,R)-lutein and (trans,R, R)-zeaxanthin and a process for the preparation thereof. The invention specifically relates to a purified xanthophyll composition comprised of more than 80% of total xanthophylls, which is further comprised of at least 80% by weight of (trans,R,R)-lutein and at least 15% by weight of (trans,R,R)-zeaxanthin. The process is comprised of mixing the concentrates containing xanthophyll esters obtained from two different plant sources in definite proportion and subjecting to treatment with alcoholic alkali, followed by neutralization and purification process to get a xanthophyll rich composition. The purification process may be comprised of treatment of crude xanthophylls with food grade solvent like ethyl acetate and washing with polar solvent to get purified xanthophyll composition selectively comprised of (trans, R,R)-lutein and (trans, R,R)-zeaxanthin. The invention relates to purified xanthophyll composition which is free from (R, S)-zeaxanthin isomer and is suitable for human consumption to be used in various eye health applications.

Objectives

The invention relates to a purified xanthophyll composition selectively comprising of (trans,R,R)-zeaxanthin along with (trans,R,R)-lutein in specific weight percentage which is prepared from xanthophyll ester concentrates of two different plant sources using food grade solvents and industrially viable process of extraction, treatment with alkali, neutralization and purification.

The main objective of this invention is to provide purified xanthophyll composition comprised of at least 80% of total xanthophylls, which is further comprised of at least 80% by weight of (trans,R,R)-lutein and at least 15% by weight of (trans,R,R)-zeaxanthin.

One more objective of the present invention is to provide purified xanthophyll rich composition comprised of selective isomers such as (trans,R,R)-zeaxanthin and (trans,R,R)-lutein and which is free from (R,S)-zeaxanthin and (S,S)-zeaxanthin isomers.

Still one more objective of the present invention is to provide a composition, which is obtained from xanthophyll ester concentrates of two different plant sources which are prepared by treatment with food grade solvent in specific proportions by using specific reaction conditions.

One more important objective of the present invention is to provide purified xanthophyll rich composition, which is prepared from xanthophyll ester concentrates of two different plant sources such as Marigold and Paprika.

One more objective of the present invention is to provide a process for preparation of xanthophyll composition, which is prepared by mixing two xanthophyll ester concentrates in definite proportion and subjecting the reaction mixture to treatment with alcoholic alkali, followed by neutralization process of xanthophylls at specific reaction conditions.

Still one more objective of the invention is to provide the process for obtaining purified xanthophyll composition which is prepared by purification of neutralized reaction mixture using food grade polar and non-polar solvents and washing to get a composition comprised of selective isomer of zeaxanthin such as (trans,R,R)-zeaxanthin.

One important objective of the present invention is to prove a purified xanthophyll composition which is suitable for human consumption to be used in various human health applications.

DETAILED DESCRIPTION

Figure 1:
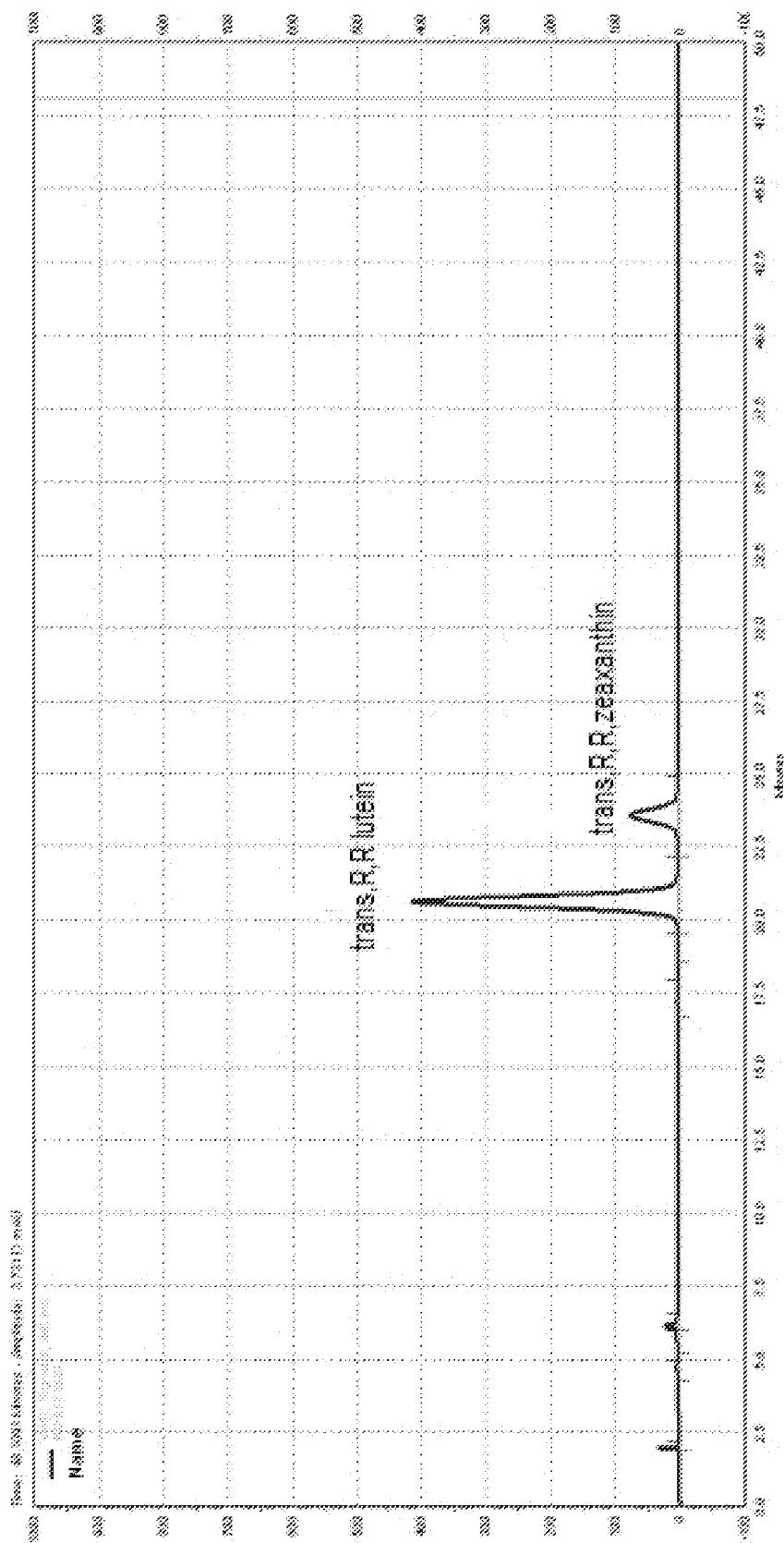
FIG. 1 depicts HPLC chromatogram of Normal phase Chromatography
Figure 2:
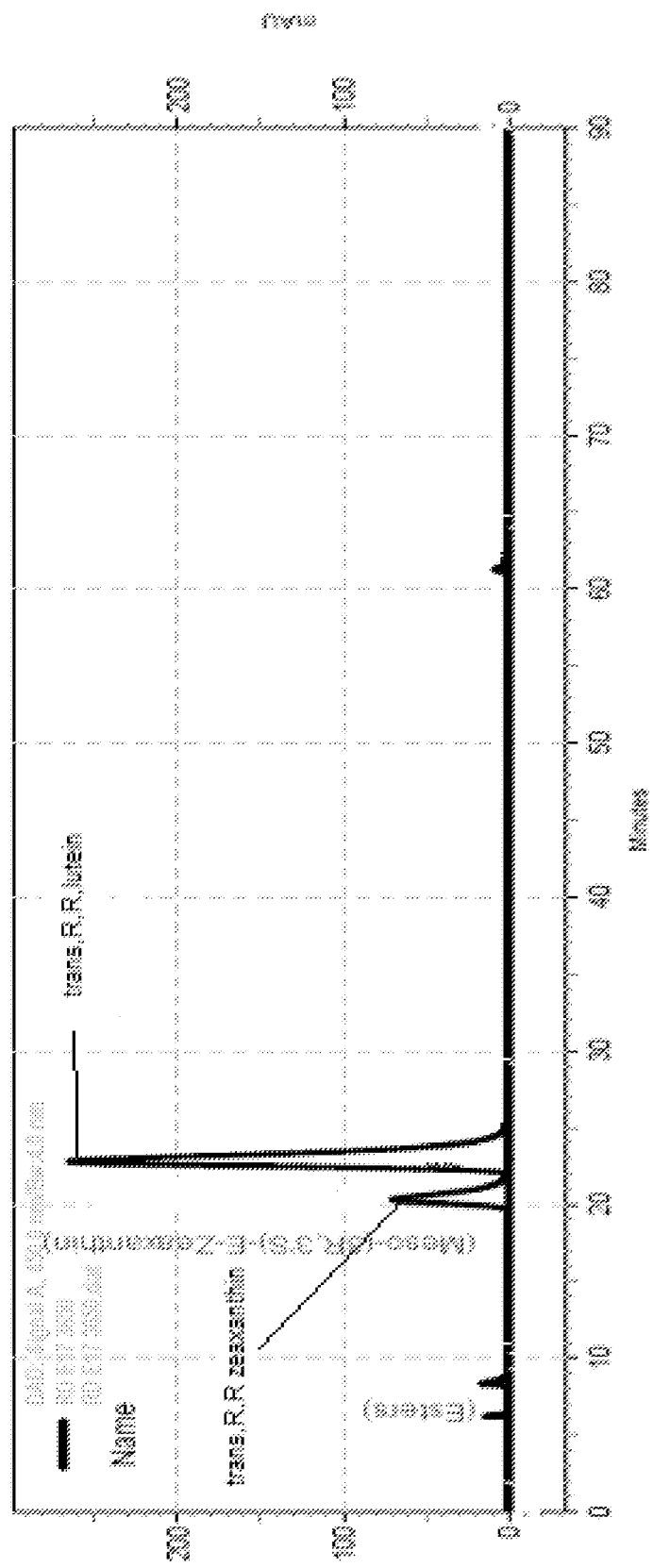
FIG. 2 depicts HPLC chromatogram of Chiral Chromatography

The invention relates to a purified xanthophyll composition comprising at least 80% by weight of total xanthophylls, which are further comprised of selective isomers such as (trans,R,R)-lutein and (trans,R,R)-zeaxanthin. The purified composition can be derived from two different plant sources by using food grade solvents and industrially viable purification process. The composition is free of (R,S)-isomer of zeaxanthin.

Within the context of this invention, the term 'purified xanthophyll composition' means a composition comprised of xanthophylls such as lutein and zeaxanthin which is prepared from xanthophyll ester concentrates of two different plant sources and purified by using food grade solvents, so that the composition is selectively comprised of (trans, R,R)-lutein and (trans,R,R)-zeaxanthin. More importantly the composition is free of (R,S)-isomer of zeaxanthin.

As used herein the term 'xanthophyll ester concentrate' means the extract obtained from the plant source with the help of treatment with organic solvents, so that the extract is rich in xanthophyll ester compounds. The concentrate is then subjected to treatment with alcoholic alkali under specific reaction conditions and temperature, followed by purification process to selectively prepare a composition containing (trans,R,R)-isomers of lutein and zeaxanthin.

The process of purification may be comprised of methods such as neutralization, washing out, precipitation and treatment with polar and non-polar solvents in order to remove unwanted impurities, waxes, fats and the like, so that the resulting composition is rich in xanthophylls such as specific isomers of lutein and zeaxanthin, which is safe and useful for human consumption. The purification processes used in instant invention are industrially viable, cost and time efficient and do not need any sophisticated equipments; but only make use of polar and non-polar solvents, which are food grade and acceptable to be used in nutraceutical or pharmaceutical applications.

According to the main embodiment of the invention, the xanthophyll composition is selectively comprised of at least 80% by weight of total xanthophylls, of which at least 80% by weight being (trans,R,R)-lutein and at least 15% by weight being (trans,R,R)-zeaxanthin which is useful for nutrition and health care.

According to important embodiment of the invention, the plant material used for the extraction may be selected from various sources including, but not limited to, fruits, flowers and vegetables such as kiwi fruit, grapes, spinach, orange juice, zucchini (or vegetable marrow), and different kinds of squash, paprika, other dark green leafy vegetables, parsley, kale, egg yolk, maize and the like. As per one of the embodiments of the invention, the plant material selected for preparation of the composition is marigold flower (*Tagetes exacta*) and hybrid species of Paprika. Particularly lutein ester concentrate is obtained from marigold flower and zeaxanthin ester concentrate is obtained from specific variety of Paprika.

As per one more embodiment of the invention, marigold flowers containing specific percentage of xanthophyll content are selected and processed to get the pellets, which are extracted using food grade solvent under specific conditions. The extract contain about 28-36% weight of lutein esters is obtained for further processing.

According to one more embodiment of the invention, fresh paprika fruit pods having (trans,R,R)-zeaxanthin content of around 0.04-0.08% by weight are selected and dried to specific moisture level and zeaxanthin content. Dried chilly (paprika) are cut in small pieces to obtain powder, which is then treated with food grade solvent/s to get extract having 3-4% by weight of (trans,R,R)-zeaxanthin. Marigold flowers (*Tagetes erecta*) is a species of the genus *Tagetes* native to Mexico. It is cultivated in Asia, Africa and South America. Marigold is also cultivated in the districts of Karnataka, particularly in the area of Hassan, Chickamangaluru, Mysore, Chamrajnagar, Davangere. For further processing the Marigold flowers are delivered to plant situated at Hassan (Karnataka) and Kangayam (Tamilnadu) India. Fresh marigold flower containing high moisture (80-90%) and xanthophyll content of around 0.1-0.2% by Weight. The flowers are then immediately taken for silaging in silos after physical cleaning under closed anaerobic conditions. Silaging is carried out for extended periods of time. The silaged flowers are subjected to industrial screw press and are squeezed for the oozing of water, bringing the moisture content from 90% to 65%, followed by drying using mechanical dryers to reduce the moisture to about 10%. Reducing the size of the dehydrated materials to obtain marigold meal with xanthophyll content of around 1.5-2.5% by weight.

The dried Marigold meal is pulverized using an industrial hammer mill and to reduce particle size. The ground Marigold meal is pelletized using an industrial pelletizer. Marigold flower pellets is extracted with hexane and are stripped for solvent to the least possible extent without much degradation to obtain marigold ester concentrate with xanthophyll content of around 14-18% by weight.

Another source used in the invention is Paprika (*Capsicum annuum*) which is a species of the plant genus *Capsicum* (peppers) native to southern North America and northern South America. This species is the most common and extensively cultivated of the five domesticated capsicums. For the purpose of present invention, the raw material may be either purchased from outside of India, or may be cultivated as *Capsicum annuum* in India. Further the Paprika variety rich in zeaxanthin may also be obtained in the form of specific breed of *Capsicum annum*.

*Capsicum annuum* is cultivated and harvested. Fresh paprika fruit pods containing high moisture (80-90%) and zeaxanthin content of around 0.04-0.08% by weight. The fruit pods are sun/mechanically dried. Moisture contents in dried paprika can range from 10 to 15% by weight. The zeaxanthin content in the ripe, dried fruit pods can be in the range of 0.4% and 0.8%.

Dried chilly is separated and cut in to small pieces to obtain powder. The dried paprika fruit pods are powdered and pelletized using an industrial pelletizer to the desired bulk density with the aid of steam/hot water as binder. Chilly pellets are extracted with hexane and acetone (75:25) to obtain paprika zeaxanthin ester concentrate with content of around 3-4% by weight.

As per one more embodiment, xanthophyll ester concentrates obtained from extraction of marigold flowers and paprika pods are mixed in suitable ratio and treated with alcoholic alkali at elevated temperature for specific time period to obtain xanthophyll reaction mixture. The alcohol can be removed and the reaction mass is mixed with water and neutralized with dilute acid to precipitate the xanthophyll mass.

As per one important embodiment, the xanthophyll mass is further subjected to purification by treatment with polar solvent followed by treatment with alcohol to obtain purified xanthophyll composition which is selectively comprised of (trans,R,R)-zeaxanthin and (trans,R,R)-lutein. This composition is free of (R,S)-zeaxanthin isomer.

According to one embodiment, xanthophyll rich composition comprising trans enriched (R,R)-isomers of lutein and zeaxanthin in specific ratio can be further formulated in different forms like powder, granules, beadlets, capsules, tablets, oil suspensions, films or any other suitable oral, parenteral or topical dosage forms using pharmaceutically or nutraceutically acceptable excipients and/or carriers.

In some embodiments, solvents employed in the extraction process to obtain lutein and zeaxanthin ester concentrates are selected from, but not limited to non-polar, semi-polar or polar solvents or combinations thereof. More preferably the solvents are selected from the group of acetone, ethyl acetate, alcohols, water, hexane and the like, either alone or in combination thereof.

As per some embodiments, xanthophyll ester concentrate is subjected to treatment with alcoholic alkali for conversion of esters into free xanthophylls at elevated temperature, wherein-alcohol used may be ethanol.

According to still one more embodiment of the invention, the elevated temperature for this treatment is above room temperature. In some embodiments, the elevated temperature ranges from about 65 to about 95° C., about 70 to about 90° C. about 70 to about 85° C., from about 75 to about 80° C., or from about 80 to about 85° C.

In certain embodiments, the ratio of alcohol to alkali ranges from about 70:30 to 90:10. In certain embodiments, the alkali is a soluble hydroxide of the alkali metals like sodium or potassium, and is selected from the group consisting of sodium hydroxide, potassium hydroxide, and mixtures thereof. In some embodiments, the alkali is sodium hydroxide. In other embodiments, the alkali is potassium hydroxide.

In certain embodiments, the ratio of xanthophyll ester concentrate to alcoholic alkali ranges from about 1:1 to about 1:2 weight/weight. In some embodiments, the ratio is about 1:1.45.

The reaction mixture obtained after treatment with alcoholic alkali can be mixed with water and then subjected to neutralization. In some embodiments, the water can be added to form the diluted resultant mixture in an amount which is about 1 to about 5 times of the reaction mixture (weight/weight). The resultant mixture can be subjected to acid treatment using dilute acid, selected from acetic acid and or hydrochloric acid. In another embodiment, the diluted acid is about 20% to about 40% of organic acid. In some embodiments, the diluted organic acid is about 20%, about 25%, about 30%, about 35%, about 40%, of organic acid.

Treatment of acid to the xanthophyll mass is used for neutralization purpose. In certain embodiments, the pH of the precipitated xanthophyll mass is maintained in the range of about 6.0 to 7.0, preferably about 6.0 to 6.5.

The xanthophyll mass is further subjected to purification with polar and non-polar solvents. In certain embodiments, the polar solvent used in the process may be selected from the group of acetone, ethyl acetate and the like or mixtures thereof. In certain embodiments, the polar solvent used to enhance purity of xanthophyll mass is ethyl acetate, which removes impurities like fatty acids, waxes, sterols and the like, that may be present in reaction mixture obtained from marigold and paprika.

After treatment with ethyl acetate, the xanthophyll crystals can be filtered and washed with water and purified with alcohols such as ethanol. In certain embodiments, the xanthophyll crystals are purified with ethanol in the ratio of about 1:3 to 1:10 w/v, about 1:3 to about 1:6, preferably in the ratio of 1:4.5 w/v. In certain embodiments, the purified xanthophyll crystals are dried under vacuum at about 50° C. to 65° C., preferably about 50° C. to 55° C., for time period ranging from 20-60 hrs, or about 20-40 hrs, preferably 30-40 hrs.

In certain embodiments, the process for preparing xanthophyll composition is comprised of following steps:

i. treating Marigold flower with suitable solvent to get xanthophyll ester concentrate;
ii. treating Paprika pods with suitable solvent to get zeaxanthin ester concentrate;
iii. mixing concentrates rich in lutein and zeaxanthin esters in the ratio of 25:75 to 50:50 to obtain blend of xanthophylls esters;
iv. treating the xanthophyll ester concentrates blend with alcoholic alkali in a ratio of about 1:2 weight/weight; at temperature about 70-85° C., preferably 80° C., for period in the range of 1 to 6 hrs, preferably 3 hrs to obtain xanthophyll mass; more preferably the ratio of xanthophyll ester blend to alcoholic alkali may lie in the range of 1:1.5 weight/weight
v. removing the aliphatic alcoholic solvent from reaction mixture under reduced pressure; followed by addition of water;
vi. neutralizing the resultant reaction mixture of step (v) by adding diluted acid;
vii. adding polar solvent followed by mixing and filtration to get precipitated xanthophyll mass;
viii. washing the residue obtained in step (vii) with water to get semi purified crystals;
ix. washing the xanthophyll crystals with ethanol in the ratio 1:4.5, filtering and drying under vacuum at 50-55° C. to for about 36 hrs obtain purified xanthophyll rich composition.

The purified xanthophyll rich composition may be comprised of at least 80% by weight of total xanthophyll, of which at least 80% by weight being (trans,R,R)-lutein and at least 15% by weight being (trans,R,R)-zeaxanthin. The composition is free of (R,S)-zeaxanthin.

In an embodiment, the purified xanthophyll rich composition is comprised of (trans,R,R)-lutein and (trans,R,R)-zeaxanthin in the ratio of 5:1.

In an embodiment, the xanthophyll composition is purified and is comprised of more than 80% of total xanthophylls as a result of extraction and purification process.

The composition of the purified xanthophyll product is analyzed by normal phase HPLC analysis with Kromasil, 4.6-mm×250-mm; 5 μm packing L3, silica column. The mobile phase used can be hexane:ethyl acetate (3:1) at a flow rate of 1.5 mL/min. UV-Vis detector set at 446 nm.

The conformation of R- and S-stereo isomers of zeaxanthin is analyzed by chiral column HPLC studies. The chiral HPLC is performed for separation and quantitation of the (trans,R,R) Zeaxanthin and (R,S)-Zeaxanthin, using CHIRALPACK AD-H 250 mm×4.6 mm, 5μ & Kromasil Silica column 4.6 mm×250 mm, 5 μm. The mobile phase can be used as gradient with combination of phase A: n-Hexane 100% and phase B: 1-Propanol:2-Propanol (50:50% V/V), at a flow rate of 0.5 mL/min. UV-Vis detector set at 450 nm.

Xanthophyll composition as such and suspended in oil in the form of oil suspension is subjected to accelerated stability condition at 25° C.±2° C./60%±5% RH and 40° C.±2° C./75%±5% RH respectively for the period of three months. The xanthophyll composition in powder form was packed in Aluminum pouch with nitrogen and oil suspension of xanthophyll composition was packed in HDPE bottles and incubated in stability chambers. The samples were analyzed for trans-lutein and (trans, R,R)-zeaxanthin content at definite time interval. It was found that the xanthophyll composition as such and in the form of oil suspension were stable over a period of three months with respect to trans lutein and zeaxanthin content. Further no physical or colour change was observed in the samples during this accelerated stability study. Thus xanthophyll composition is stable over various storage conditions and also in the form of different dosage form. According to still one more embodiment of the invention, xanthophyll composition described herein can be formulated using at least one pharmaceutical, nutraceutical or food grade excipient. The excipient can be a carrier, granulating agent, inert core, coating agent, solvent, diluents, binder, lubricant, disintegrant, antioxidant, oil, surfactant, solubilizer, emulisifer or any other excipient, which is known to a person skilled in the art as excipient required for preparing palatable dosage form, acceptable to the subject.

The details of the present invention are described in the examples given below which are provided to illustrate the invention and therefore should not be construed to limit the scope of the present invention.

EXAMPLES

Example 1

A weighed quantity of marigold pellets (1000 gm) with a xanthophyll content 2.4% (by spectrophotometric method) was transferred into a round bottom flask followed by the addition of 5000 ml of hexane. The pellets were extracted at room temperature for 60 min and repeated for 3 to 4 times to extract the xanthophylls completely. The extracted layer was pooled and concentrated under reduced pressure to obtain xanthophyll ester concentrate. The yield of the concentrate was 150 g (15%). Xanthophyll content was 15.68% by weight (by UV/Vis spectrophotometry). The recovery of xanthophylls was more than 98%.

Example 2

A weighed quantity of paprika pellets (1000 gm) with a xanthophyll content 1.12% (by spectrophotometric method) and 0.4% zeaxanthin content (by HPLC method) was transferred into a round bottom flask followed by the addition of mixture of 25:75 acetone and hexane (720 ml:2250 ml). The pellets were extracted at room temperature for 60 min and repeated to 5 times to extract the xanthophylls completely. The extracted layer was pooled and concentrated under reduced pressure to obtain zeaxanthin rich ester concentrate. The yield of the ester concentrate was 80 g (8%). Xanthophyll content was 7.03% by weight (by UV/Vis spectrophotometry) and zeaxanthin content was 4.38% (by HPLC method). The recovery of zeaxanthin was more than 85%.

Example 3

Commercial grade marigold concentrate (70 g) containing 16.27% xanthophyll content (by spectrophotometric method) and paprika concentrate (30 g) containing 5.29% xanthophyll content (by spectrophotometric method) and 3.13% zeaxanthin content (by HPLC method) was transferred in to a round bottom flask and mixed thoroughly. The xanthophyll content of the mixture was 13.13% (by spectrophotometric method). Aqueous alcoholic alkali solution (20 gm potassium hydroxide in 30 ml water and 125 ml of ethanol) was added, the mixture was heated in an oil bath with stirring at 80° C. for a period of 4 hours. The degree of hydrolysis was monitored by HPLC during the reaction. Ethanol was distilled off under reduced pressure and the solids obtained were stirred with 200 ml of water at room temperature. The resultant mixture was neutralized with diluted 25% of aqueous acetic acid solution to get pH 6.5. Ethyl acetate (400 ml) was added and the resultant mixture filtered through Buchner funnel to get crude cake (30 g). The crude cake obtained was washed three times with 12 volumes each of distilled water for removing the impurities and to get semi-purified crystals of xanthophyll composition. These semi-purified crystals obtained (25 g) were subjected to further purification by stirring with 4.5 volumes of ethanol at room temperature, followed by filtration. The resulting crystals were vacuum dried at temperature of about 50 to 55° C. for 36 hrs. The yield of the dried xanthophyll crystals was 12.43 g (12.43%). The xanthophyll content was 82.07% by weight (UV/Vis spectrophotometry) out of which the contents of (trans,R,R)-lutein and (trans,R,R)-zeaxanthin were 80.57%, and 16.47% respectively as determined by normal phase HPLC analysis.

Chiral chromatography analysis of purified xanthophylls confirmed the absence of (R,S) & (S,S)-zeaxanthin.

Example 4

Commercial grade marigold concentrate (70 g) containing 15.26% xanthophyll content (by spectrophotometric method) and paprika concentrate (30 g) containing 5.57% xanthophyll content (by spectrophotometric method) and 3.45% zeaxanthin content (by HPLC method) was transferred in to a round bottom flask and mixed thoroughly. The xanthophyll content of the mixture was 12.54% (by spectrophotometric method). Aqueous alcoholic alkali solution (20 gm potassium hydroxide in 30 ml water and 125 ml of ethanol) was added, the mixture was heated in an oil bath with stirring at 80° C. for a period of 4 hours. The degree of hydrolysis was monitored by HPLC during the reaction. Ethanol was distilled off under reduced pressure and the solids obtained were stirred with 200 ml of water at room temperature. The resultant mixture was neutralized with diluted 25% of aqueous acetic acid solution to get pH 6.5, ethyl acetate (400 ml) was added and the resultant mixture filtered through Buchner funnel to get crude cake (32 g). The crude cake obtained was washed three times with 12 volumes each of distilled water for removing the impurities and to get semi-purified crystals of xanthophyll composition. The semi-purified crystals obtained (24 g) were subjected to further purification by stirring with 4.5 volumes of ethanol at room temperature, followed by filtration. The resulting crystals were vacuum dried at temperature of about 50 to 55° C. for 36 hrs. The yield of the dried xanthophyll crystals was 12.52 g (12.52%). The xanthophyll content was 82.07% by weight (UV/Vis spectrophotometry) out of which the contents of (trans,R,R)-lutein and (trans,R,R)-zeaxanthin were 81.12%, and 15.12% respectively as determined by normal phase HPLC analysis.

Chiral chromatography analysis of purified xanthophylls confirmed the absence of (R,S) & (S,S)-zeaxanthin.

Example 5

Commercial grade marigold concentrate (350 g) containing 15.14% xanthophyll content (by spectrophotometric method) and paprika concentrate (150 g) containing 5.84% xanthophyll content (by spectrophotometric method) and 3.59% zeaxanthin content (by HPLC method) was transferred in to a round bottom flask and mixed thoroughly. The xanthophyll content of the mixture was 12.07% (by spectrophotometric method). Aqueous alcoholic alkali solution (100 gm potassium hydroxide in 150 ml water and 625 ml of ethanol) was added, the mixture was heated in an oil bath with stirring at 80° C. for a period of 4 hours. The degree of hydrolysis was monitored by HPLC during the saponification stage. Ethanol was distilled off under reduced pressure and the solids obtained were stirred with 1000 ml of water at room temperature. The resultant mixture was neutralized with diluted 25% of aqueous acetic acid solution to get pH 6.5, ethyl acetate (2000 ml) was added and the resultant mixture filtered through Buchner funnel to get crude cake (154 g). The crude cake obtained was washed three times with 12 volumes each of distilled water for removing the impurities and to get semi-purified crystals of xanthophyll composition. This semi-purified crystals obtained (122 g) were subjected to further purification by stirring with 4.5 volumes of ethanol at room temperature, followed by filtration. The resulting crystals were vacuum dried at temperature of about 50 to 55° C. for 36 hrs. The yield of the dried xanthophyll crystals was 64.05 g (12.81%). The xanthophyll content was 81.28% by weight (UV/Vis spectrophotometry) out of which the contents of (trans,R,R)-lutein and (trans, R,R)-zeaxanthin were 81.19%, and 15.24% respectively as determined by normal phase HPLC analysis.

Chiral chromatography analysis of purified xanthophylls confirmed the absence of (R,S) & (S,S)-zeaxanthin.

Example 6

Commercial grade marigold concentrate (130 g) containing 15.26% xanthophyll content (by spectrophotometric method) and paprika concentrate (70 g) containing 5.57% xanthophyll content (by spectrophotometric method) and 3.45% zeaxanthin content (by HPLC method) was transferred in to a round bottom flask and mixed thoroughly. The xanthophyll content of the mixture was 12.54% (by spectrophotometric method). Aqueous alcoholic alkali solution (40 gm potassium hydroxide in 60 ml water and 250 ml of ethanol) was added, the mixture was heated in an oil bath with stirring at 80° C. for a period of 4 hours. The degree of hydrolysis was monitored by HPLC during the saponification stage. Ethanol was distilled off under reduced pressure and the solids obtained were stirred with 400 ml of water at room temperature. The resultant mixture was neutralized with diluted 25% of aqueous acetic acid solution to get pH 6.5, ethyl acetate (800 ml) was added and the resultant mixture filtered through buchner funnel to get crude cake (59 g). The crude cake obtained was washed three times with 12 volumes each of distilled water for removing the impurities and to get semi-purified crystals of xanthophyll composition. This semi-purified crystals obtained (48 g) was subjected to further purification by stirring with 4.5 volumes of ethanol at room temperature, followed by filtration. The resulting crystals were vacuum dried at temperature of about 50 to 55° C. for 36 hrs. The yield of the dried xanthophyll crystals was 26.24 g (13.12%). The xanthophyll content was 82.64% by weight (UV/Vis spectrophotometry) out of which the contents of (trans,R,R)-lutein and (trans,R,R)-zeaxanthin were 80.67%, and 15.43% respectively as determined by normal phase HPLC analysis.

Chiral chromatography analysis of purified xanthophylls confirmed the absence of (R,S) & (S,S)-zeaxanthin.

Example 7

Commercial grade marigold concentrate (130 g) containing 15.44% xanthophyll content (by spectrophotometric method) and paprika concentrate (70 g) containing 4.38% xanthophyll content (by spectrophotometric method) and 3.45% zeaxanthin content (by HPLC method) was transferred in to a round bottom flask and mixed thoroughly. The xanthophyll content of the mixture was 13.14% (by spectrophotometric method). Aqueous alcoholic alkali solution (40 gm potassium hydroxide in 60 ml water and 250 ml of ethanol) was added, the mixture was heated in an oil bath with stirring at 80° C. for a period of 4 hours. The degree of hydrolysis was monitored by HPLC during the saponification stage. Ethanol was distilled off under reduced pressure and the solids obtained were stirred with 400 ml of water at room temperature. The resultant mixture was neutralized with diluted 25% of aqueous acetic acid solution to get pH 6.5, ethyl acetate (800 ml) was added and the resultant mixture was filtered through Buchner funnel to get crude cake (62 g). The crude cake obtained was washed three times with 12 volumes each of distilled water for removing the impurities and to get semi-purified crystals of xanthophyll composition. The semi-purified crystals obtained (45 g) were subjected to further purification by stirring with 4.5 volumes of ethanol at room temperature, followed by filtration. The resulting crystals were vacuum dried at temperature of about 50 to 55° C. for 36 hrs. The yield of the dried xanthophyll crystals was 26.24 g (13.12%). The xanthophyll content was 83.04% by weight (UV/Vis spectrophotometry) out of which the contents of (trans,R,R)-lutein and (trans, R,R)-zeaxanthin were 72.86%, and 18.83% respectively as determined by normal phase HPLC analysis.

Chiral chromatography analysis of purified xanthophylls confirmed the absence of (R,S) & (S,S)-zeaxanthin.

The invention claimed is:

1. A purified xanthophyll composition comprising about 80% by weight of (trans, R,R)-lutein and about 15% by weight of (trans, R,R)-zeaxanthin, wherein the composition is free from (R, S)-zeaxanthin and (S,S)-zeaxanthin isomers, said composition prepared by a process of comprising:
   a. extracting two different plant sources separately with food grade solvents to obtain xanthophyll ester concentrates;
   b. mixing two xanthophyll ester concentrates in definite proportions to obtain a mixture;
   c. reacting the mixture with an alcoholic alkali solution at specific temperature for 1-6 hours;
   d. removing alcohol under reduced pressure and mixing with water to obtain a reaction mass;
   e. neutralizing the reaction mass with dilute acid and mixing with ethyl acetate;
   f. filtering to obtain partially purified xanthophyll product;
   g. washing the product with water followed by alcohol to obtain the purified xanthophyll composition;
   h. drying the purified xanthophyll composition under vacuum at specific temperature;
   wherein the two different plant sources are marigold and paprika; and
   wherein marigold is the plant source for lutein and paprika is the plant source for zeaxanthin.

2. The purified xanthophyll composition as claimed in claim 1, which is comprised of more than 80% of xanthophylls.

3. The purified xanthophyll composition according to claim 1, wherein the process comprises:
   a. treating marigold flowers and paprika separately with food grade solvents selected from the group consisting of a polar solvent, a non polar solvents, and a mixture thereof to obtain the concentrates rich in xanthophyll esters;
   b. mixing the concentrates of marigold and paprika rich in esters of lutein and zeaxanthin, respectively, in proportions ranging from 50:50 to 90:10 to obtain a concentrate mixture;
   c. reacting the concentrate mixture with an alcoholic alkali solution at temperature ranging from 70° C. to 85° C. for 1-6 hours;
   d. removing alcohol under reduced pressure and mixing with water to obtain a reaction mass;
   e. neutralizing the reaction mass with dilute acetic acid or dilute hydrochloric acid, and further mixing with ethyl acetate to obtain partially purified xanthophyll product;
   f. washing the product with water and filtering out xanthophylls crystals;
   g. treating the xanthophylls crystals with alcohol to obtain purified xanthophylls;
   h. drying the purified xanthophylls under vacuum at 50° C.-55° C. for 20-60 hours to obtain the composition.

4. The xanthophyll composition according to claim 3, wherein the non polar solvents is selected from the group consisting of acetone, hexane, ethyl acetate, water, or a mixture thereof.

5. The purified xanthophyll composition according to claim 3, wherein step (c) comprises reacting the concentrate mixture with the alcoholic alkali solution in a proportion ranging from 1:1 to 1:2.

6. The purified xanthophyll composition according to claim 5, wherein the alcoholic alkali solution comprises sodium hydroxide in an alcohol selected from the group consisting of methanol, ethanol, and isopropanol.

7. The purified xanthophyll composition according to claim 5, wherein the alcoholic alkali solution comprises potassium hydroxide in an alcohol selected from methanol, ethanol, and isopropanol.

8. The purified xanthophyll composition according to claim 3, wherein step (g) comprises treating the xanthophyll crystals with ethanol in a ratio ranging from 1:3 to 1:10.

9. The purified xanthophyll composition of claim 1, wherein the composition is suitable for human consumption.

* * * * *